United States Patent [19]

Wright

[11] Patent Number: 4,496,569

[45] Date of Patent: Jan. 29, 1985

[54] ANTIALLERGIC (1H-TETRAZOL-5-yl)TETRAZOLO[1,5-a]QUINOLINES AND DERIVATIVES THEREOF

[75] Inventor: Terry L. Wright, Clayton, Calif.

[73] Assignee: The Dow Chemical Company, Midland, Mich.

[21] Appl. No.: 478,964

[22] Filed: Mar. 25, 1983

[51] Int. Cl.³ .................... A61K 31/47; A61K 31/44; C07D 471/04; C07D 471/14
[52] U.S. Cl. .................... 514/311; 514/381; 514/312; 514/314; 546/122; 546/176; 546/65; 546/82
[58] Field of Search .................... 546/82, 65; 424/258, 424/256

[56] References Cited

U.S. PATENT DOCUMENTS 3,764,681 10/1973 Dreikorn .................... 424/258

OTHER PUBLICATIONS

Fieser, M., et al., *Reagents For Organic Synthesis*, vol. 2, Wiley-Interscience, NY, 1969, p. 376.
Chemical Abstracts, 88:137453m (1978)[Ger. Offen. 2,731,323, Illy, 1/26/78].
Meth-Cohn, O., et al., *J. Chem. Soc. Perkin Trans I*, 2509-2517 (1981).
Reimlinger, H., et al., *Chem. Ber.* 108, 3780-3786 (1975).
Livi, O., et al. *Il Farmaco, Ed. Sci.*, 30 (12), 1017 (1975).
Ferrarini, P., et al., *Il Farmaco, Ed. Sci.*, 33 (7), 543 (1978).
Erickson, E., et al., *J. Med. Chem.*, 22 (7), 816-823 (1979).

*Primary Examiner*—Richard A. Schwartz
*Attorney, Agent, or Firm*—John J. Kolano; Gary D. Street; Richard G. Waterman

[57] ABSTRACT (1H-Tetrazol-5-yl)tetrazolo[1,5-a]quinolines and related compounds which are useful as antiallergic agents are described herein. The compounds are prepared by the reaction of an appropriate halocyanoquinoline or isoquinoline with ammonium chloride and an azide such as sodium azide in an inert solvent such dimethylformamide.

13 Claims, No Drawings

ANTIALLERGIC (1H-TETRAZOL-5-YL)TETRAZOLO[1,5-A]QUINO- LINES AND DERIVATIVES THEREOF

The present invention relates to a group of compounds containing two tetrazole rings with one of the tetrazole rings fused into a tricyclic system and the second being a substituent on that ring system. More particularly, the present invention relates to compounds having the following general formula:

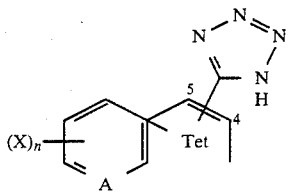

wherein Tet is the divalent tetrazolo group of the formula

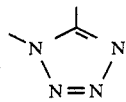

which is attached to the ring system to give either isomeric form; A is —CH= or —N=; n is 0, 1 or 2; X is H, alkyl or 1-4 C, alkoxy or 1-4 C, halogen, methylmercapto, methylsulfonyl, or two X's can be combined as methylenedioxy; with the proviso that, when X is methylmercapto or methylsulfonyl, then n must be 1; and the pharmaceutically acceptable salts thereof.

The substituent with the free valence entering the ring between the positions marked as 4 and 5 can only be attached to either of those two positions. The X substituent can only be attached at available 7-, 8- and/or 9-positions in the left hand ring in the structure shown above. Halogen is fluorine, chlorine or bromine. Examples of the alkyl groups are methyl, ethyl, propyl and isopropyl; examples of the alkoxy groups are methoxy, ethoxy, propoxy, isopropoxy and butoxy.

Particularly preferred compounds are those having the following general formula:

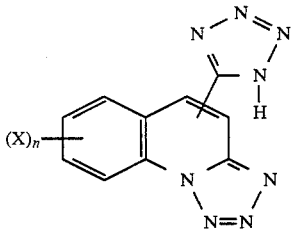

wherein $(X)_n$ is defined as above; and the pharmaceutically acceptable salts thereof.

Equivalent to the above tetrazoles for the purposes of this invention are the pharmaceutically acceptable salts and also the hydrates of the compounds and their salts. The term "pharmaceutically acceptable salt" as used herein is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine, tri-n-butylamine, tromethamine, triethanolamine and N-methylglucamine. While the indicated salts can be considered as equivalent to the tetrazoles as far as pharmacological effects are concerned, certain of these salts have the further advantage of better physical properties. Thus, for example, they give solid forms which can be handled much more easily than the tetrazole itself.

The compounds of the present invention are prepared from a halocyanide of the formula:

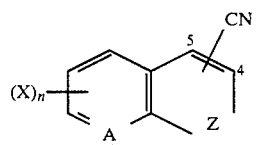

wherein —CN is substituted at the 4- or 5-position; $(X)_n$ is defined as above and Z is —N=C(Hal)—, wherein Hal is chlorine or bromine, in either isomeric form. The halocyanide is heated with ammonium chloride and sodium azide in an inert solvent such as dimethylformamide. Although the chlorocyanide is preferred in the procedure above, the corresponding bromocyanide can also be used. Similarly, sodium azide is the preferred azide although other alkali metal azides could also be used.

Where the starting material above is a 2-chloro-3-cyanoquinoline, this can be prepared by starting from an appropriate substituted acetanilide. This is heated with phosphoryl chloride and dimethylformamide to give the corresponding 2-chloro-3-quinolinecarboxaldehyde. The process involved is discussed in detail by meth-Cohn et al., J. Chem. Soc., Perkin Trans. 1, 1981, 1520. The chloroquinolinecarboxaldehyde is then reacted with hydroxylamine hydrochloride, formic acid and sodium formate with heating to give the corresponding 3-cyano-2(1H)-quinolinone. This is then heated with an excess of phosphoryl chloride to give the desired 2-chloro-3-cyanoquinoline.

Alternatively, it is possible to obtain the desired 2-chloro-3-cyanoquinoline directly from an appropriate acetanilide. The acetanilide is heated with dimethylformamide and phosphorus oxychloride and, after the initial reaction is complete, hydroxylamine (hydrochloride) is added to the reaction mixture and the product indicated earlier is isolated. Thus, cyclization to a quinoline takes place and a cyano substituted product is obtained.

While all of the basic reactants are the same, this procedure for preparing the cyano compounds differs from that described earlier in that the reaction is not carried out stepwise with isolation of some type of product after each step of the procedure. With this difference in procedures, the actual series of reactants involved in the two procedures is not identical. Thus, with acetanilide as the starting material, the reaction with dimethylformamide and phosphoryl chloride actually gives, in solution, the cyclized quinoline with a 3-iminium [—CH=N$^\oplus$<], substituent. This iminium (salt) can actually be used as such in solution without resorting to isolation wherein the iminium is changed to the corresponding (quinoline)-3-carboxaldehyde. In the stepwise procedure, the carboxaldehyde is reacted with hydroxylamine to give the oxime which is then dehydrated to the nitrile but, in the course of this reaction in the quinoline procedure under consideration here, the 2-chloro substituent is hydrolyzed to a ketone and an additional separate step is needed to get back to 2-chloro-substitution. In contrast, in the one-step procedure, the iminium salt can be considered as an aldehyde equivalent and it reacts directly with hydroxylamine to give the oxime. But, since an excess of dehydrating agent is present (phosphoryl chloride), the oxime is immediately dehydrated to the nitrile without affecting the 2-chloro atom. Although the procedure is described above for an aldehyde equivalent (iminium salt), it is possible to carry out the same process on aldehydes too. That is, reaction of an aldehyde with phosphorus oxychloride and hydroxylamine also gives a nitrile directly.

The method above can be generalized to provide a process for the general conversion of an aldehyde or an aldehyde equivalent (such as an iminium salt) to the corresponding nitrile by reaction with hydroxylamine and phosphoryl chloride. The process as described herein can be further generalized to include the immediately preceding step of the formation of an aldehyde or aldehyde equivalent as obtained in the synthesis of the iminium intermediates used in the present application or aldehydes as obtained from an aromatic compound by a Vilsmeier-type reaction.

The tetrazoles of the present invention are converted to the corresponding pharmaceutically acceptable salts by reacting them with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Penna.

The compounds of the present invention or pharmaceutical compositions thereof may be administered to human asthmatic patients in single oral doses of approximately 1-1000 mg of active ingredient and multiple oral doses totaling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5-14 days with food and water ad lib.
3. Sensitization—Recipient rats were passively sensitized by the intradermal injection of 100 microliters of two dilutions of antiserum (one injection on each side of the back). Sensitization occurred 48-72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge or p.o. at 100 mg/kg 5 to 240 minutes prior to challenge.
5. Antigen Challenge and Reaction Evaluation—Ovalbumin (0.1-1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both i.p. and orally.

In addition to activity in the PCA test as described above, the compounds of the present invention also inhibit the release of histamine in the rat Passive Peritoneal Anaphylaxis (PPA) test. This method can be described briefly as follows:

PPA Test Method

1. Antisera—Reaginic antibody to ovalbumin for this test was prepared in adult male $B_6D_2F_1$ mice.
2. Animals Adult male Sprague Dawley or female Wistar Kyoto rats were used as antibody recipients. The animals were allowed to acclimate for 5–14 days with food and water ad lib.
3. Sensitization—Recipient rats were sensitized i.p. with 2 ml of an appropriate saline dilution of the mouse anti-ovalbumin antiserum determined from prior experiments. Sensitization took place 2 hours prior to antigen challenge.
4. Administration of Test Compound—Five to ten animals were used for each test compound/dilution. Compounds were homogenized in saline with an equivalent of sodium bicarbonate to effect solubilization, if appropriate, and administered i.p. at 60 µg, 30 seconds prior to antigen challenge or p.o. 5 to 60 minutes prior to antigen challenge.
5. Antigen Challenge and Assay Evaluation—Two mg of ovalbumin in 5 ml of modified Tyrode's Solution was administered by i.p. injection and the animals were sacrificed 5 minutes later. Peritoneal shock fluids were collected and classified by centrifugation. Protein was removed from the samples by perchloric acid precipitation and subsequent centrifugation. The samples were then analyzed for histamine content by an automated fluorometric assay. Histamine levels of peritoneal shock fluids from treatment animals were then compared to those of shock fluids from control animals. Drug effect was expressed as percent inhibition of histamine release.

The following examples are presented to illustrate the present invention but they should not be construed as limiting in any way.

EXAMPLE 1

To a mixture of 11880 ml of phosphoryl chloride and 2500 g of acetanilide was added, with cooling and stirring in an ice bath, 3380 g of dimethylformamide at such a rate that the temperature did not exceed 60° C. The addition took about 45 minutes, at which time the cooling bath was removed and the mixture was heated to 75° C. for 22 hours. The mixture was then cooled and the excess phosphoryl chloride was removed by rotary evaporation. The residual dark brown oil was then poured into about 32 liters of water with stirring. Ice was added to the aqueous mixture to keep the temperature below 50° C. The dark yellow solid which formed was separated by filtration and dried in a forced-air oven at 70° C. to give 2-chloro-3-quinolinecarboxaldehyde melting at about 145°–147° C.

EXAMPLE 2

To the mixture obtained by the addition of 210 g of 4-(methylthio)acetanilide to 1246 g of phosphoryl chloride there was added 254 g of dimethylformamide over a period of 30 minutes with stirring. The reaction was exothermic and the rate of addition was controlled so that the temperature did not exceed 75° C. After the addition was complete, the reaction was heated at 75° C. for 2.5 hours. The mixture was then quenched in water and the yellow precipitate which formed was separated by filtration and dried to give 2-chloro-6-methylthio-3-quinolinecarboxaldehyde.

When the above procedure was repeated using 3,4-dimethoxyacetanilide, the procedure obtained was 2-chloro-6,7-dimethoxy-3-quinolinecarboxaldehyde.

EXAMPLE 3

A mixture was prepared from 6 liters of 97% formic acid, 300 g of hydroxylamine hydrochloride, 500 g of sodium formate, and 700 g of 2-chloro-3-quinolinecarboxaldehyde and this mixture was heated to reflux (110° C.). The resulting solution was then maintained at 110° C. for 18 hours. The solution was then cooled and the solid which crystallized was separated by filtration and then successively washed twice with water, once with ethanol and once with methylene chloride to give 3-cyano-2(1H)-quinolinone.

EXAMPLE 4

A mixture was prepared from 15 g of 2-chloro-6,7-dimethyl-3-quinolinecarboxaldehyde, 5.4 g of hydroxylamine hydrochloride, 8.5 g of sodium formate and 155 ml of 97% formic acid and this was heated at reflux for 3 hours. Initially, the mixture became a heavy yellow paste but a homogeneous brown solution formed later. However, by the end of the 3-hour reflux period, the mixture was again heterogeneous and it was cooled and poured into 300 ml of water. The solid which formed was separated by filtration and dried to give 3-cyano-6,7-dimethyl-2(1H)-quinolinone melting at about 300° C. The indicated product contained ¼ molecule of water of hydration.

When the above procedure was repeated using the appropriate starting materials, the following compounds were obtained:

3-Cyano-6,7-dimethoxy-2(1H)-quinolinone (¼H$_2$O) melting at greater than 300° C.

3-Cyano-6-methylthio-2(1H)-quinolinone (1/6 H$_2$O) melting at about 287°–288° C.

EXAMPLE 5

To a solution of 10 ml of 30% hydrogen peroxide and 100 ml of acetic acid there was added 4.0 g of 3-cyano-6-methylthio-2(1H)-quinolinone and the mixture was heated at reflux for 1.5 hours. A homogeneous solution formed initially but, during the course of the reaction, a light yellow precipitate appeared. The mixture was cooled and the solid was separated by filtration to give 3-cyano-6-methylsulfonyl-2(1H)-quinolinone melting at greater than 310° C.

EXAMPLE 6

A mixture of 50 g of 3-cyano-2(1H)-quinolinone and 250 ml of phosphoryl chloride was heated at reflux for 18 hours. Volatile material was evaporated from the mixture under reduced pressure and the resulting residue was carefully added to water. The solid which formed was separated by filtration, washed with water and dried to give crude product. This was dissolved in methylene chloride and the resulting solution was treated with silica gel and filtered to give a pale yellow solution. Hexane was added to the solution which was then placed on a steam bath until crystallization occurred. The solid was then separated by filtration to give 2-chloro-3-cyanoquinoline. This compound melts at about 163°–164° C.

EXAMPLE 7

A mixture was prepared from 67.5 g of 3-cyano-6,7-dimethyl-2(1H)-quinolinone and 340 ml of phosphoryl chloride and this was heated at reflux for 18 hours. The mixture was cooled, excess phosphoryl chloride was removed by vacuum evaporation, and the residue was carefully added to water with vigorous stirring. The solid which formed was separated by filtration and recrystallized from methylene chloride to give 2-chloro-3-cyano-6,7-dimethylquinoline melting at about 189°–190° C.

When the above procedure was repeated using the appropriate starting materials, the following compounds were obtained:

2-Chloro-3-cyano-6,7-dimethoxyquinoline.

2-Chloro-3-cyano-6-(methylthio)quinoline melting at about 227°–228° C.

2-Chloro-3-cyano-6-methylsulfonylquinoline melting at about 233°–235° C.

EXAMPLE 8

To a mixture of 118 ml of phosphoryl chloride and 25 g of acetanilide was added, with cooling and stirring in an ice bath, 41 g of dimethylformamide at such a rate that the temperature did not exceed 75° C. After the addition was complete, a heat lamp was applied and the temperature was maintained at 75° C. for 20 hours. Heating was then stopped and the mixture was allowed to cool for a few minutes and the temperature fell to 62° C. Hydroxylamine hydrochloride (14 g) was added all at once to the stirred mixture. After about 2–3 minutes, a slow exothermic reaction started and the mixture began to boil with considerable gas evolution. The temperature rose slowly from 62° C. to 77° C. over a period of about 15 minutes. By this time, gas evolution had almost stopped. The mixture was then allowed to cool to room temperature and a heavy solid precipitated. The mixture was then quenched carefully by the addition of 1000 ml of water with vigorous stirring. The solid was then separated by filtration and dissolved in methylene chloride and the methylene chloride solution was treated with charcoal filtered, concentrated and cooled. Filtration then gave light yellow crystals of 2-chloro-3-cyanoquinoline.

EXAMPLE 9

A mixture was prepared from 10 g of 2-chloro-3-quinolinecarboxaldehyde, 5.2 g of hydroxylamine hydrochloride and 100 ml of phosphoryl chloride and heated with a heat lamp. The mixture was heterogeneous until the temperature reached 90° C. and there was no noticeable exotherm or gas evolution. After heating at reflux for 30 minutes, the mixture was cooled for 16 hours. It was then quenched in 700 ml of water. The tan solid which formed was separated by filtration and dried to give 7 g of crude 2-chloro-3-cyanoquinoline.

EXAMPLE 10

To a solution of 10.0 g of 2-bromo-4-cyanoquinoline in 150 ml of dimethylformamide was added 5.3 g of ammonium chloride and 6.5 g of sodium azide. The heterogeneous mixture was heated at 120° C. for 16 hours and then cooled and filtered to remove the solid present. The filtrate was poured into 500 ml of water and acidified with concentrated hydrochloric acid. A heavy creamy white precipitate formed and this was separated by filtration and dried. The solid was then redissolved in aqueous base and the alkaline solution was extracted with methylene chloride to remove any insoluble material. The aqueous solution was then acidified by the addition of hydrochloric acid and the precipitate which formed was separated by filtration to give 5-(1H-tetrazol-5-yl)tetrazolo[1,5-a]quinoline melting at about 250°–251° C. with decomposition.

EXAMPLE 11

A mixture of 7.0 g of 2-chloro-3-cyano-1,8-naphthyridine, 4.4 g of ammonium chloride and 5.3 g of sodium azide in 200 ml of dimethylformamide was heated at 120° C. for 16 hours. The mixture was then poured into 600 ml of water and acidified to a pH of 2 by the addition of concentrated hydrochloric acid. The precipitate which formed was separated by filtration and added to 1500 ml of aqueous 1N sodium hydroxide solution. It was necessary to heat the mixture to 45° C. in order to obtain a homogeneous solution. The solution was then treated with charcoal and filtered through Celite to give a light yellow solution. Acidification of this solution gave a pale yellow-white solid which was separated and dried to give 4-(1H-tetrazol-5-yl)tetrazolo[1,5-a][1,8]naphthyridine melting at about 280°–282° C. with decomposition.

EXAMPLE 12

A mixture of 6.6 g of 2-chloro-3-cyanoquinoline, 5.0 g of sodium azide and 4.2 g of ammonium chloride in 100 ml of dimethylformamide was heated at 120° C. for 17 hours. The mixture was poured into 500 ml of water and then acidified to a pH of 2 with hydrochloric acid. A heavy yellow precipitate formed and was separated by filtration. The solid was then redissolved in aqueous base, using about 1500–2000 ml of water because of the low solubility of the sodium salt. Concentrated hydrochloric acid was then added to the clear yellow solution until a pH of 2 was obtained. A heavy precipitate formed and this was separated by filtration and dried to give 4-(1H-tetrazol-5-yl)tetrazolo[1,5-a]quinoline melting at about 280°–282° C. with decomposition. This compound has the following structural formula:

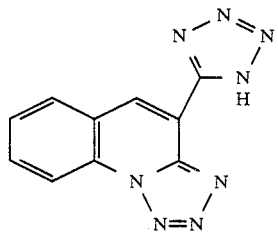

EXAMPLE 13

The procedure of the preceding example was repeated using the appropriate substituted quinoline but the redissolving and reprecipitation of the product was omitted. The following compounds were obtained:

7,8-Dimethyl-4-(1H-tetrazol-5-yl)tetrazolo[1,5-a]quinoline (containing ¼ mole of water of hydration) melting at about 284°–286° C. with decomposition.

7.8-Dimethoxy-4-(1H-tetrazol-5-yl)tetrazolo[1,5-a]quinoline (containing 1.5 mole of water of hydration) melting at about 275°–276° C. with decomposition.

7-Methylsulfonyl-4-(1H-tetrazol-5-yl)tetrazolo[1,5-a]quinoline melting at about 274°–275° C. with decomposition.

7-Methylthio-4-(1H-tetrazol-5-yl)tetrazolo[1,5-a]quinoline melting at about 269°–271° C. with decomposition.

7-Chloro-4-(1H-tetrazol-5-yl)tetrazolo[1,5-a]quinoline is also obtained in the same way, with the starting material obtained by the procedures of Examples 4 and 7.

EXAMPLE 14

A mixture of 7.0 g of 1-chloro-4-cyanoisoquinoline, 4.3 g of ammonium chloride, 5.3 g of sodium azide and 100 ml of dimethylformamide was heated at 120° C. for 16 hours. The mixture was poured into 600 ml of water and acidified to a pH of 2 with hydrochloric acid. The cream colored precipitate which formed was separated by filtration and dried and then recrystallized from dimethylsulfoxide to give 5-(1H-tetrazol-5-yl)tetrazolo[5,1-a]isoquinoline hemihydrate melting at about 235°–250° C. decomposition.

EXAMPLE 15

A mixture of 128 g of 2-chloro-3-cyanoquinoline, 80 g of ammonium chloride, and 97 g of sodium azide in 1800 ml of dimethylformamide was heated at 110° C. for 15 hours. The mixture was then poured into 4 liters of water. The resulting, almost homogeneous, solution was then stirred and acidified with concentrated hydrochloric acid to pH 2. The heavy precipitate which formed was separated by filtration and, while still wet, it was added to 4 liters of water containing 1.1 equivalents (based on theoretical yield) of sodium hydroxide. The resulting aqueous mixture was then heated to about 50°–60° C. but showed no signs of becoming homogenous. The mixture (in 2 portions) was then diluted with water to a total volume of 8 liters and heated to 80° C. The solutions were treated with charcoal and filtered through Celite to give pale yellow filtrates. These were combined and cooled for 16 hours. The solid which formed was then separated by filtration to give the sodium salt of 4-(1H-tetrazol-5-yl)tetrazolo[1,5-a]quinoline.

EXAMPLE 16

4-(1H-Tetrazol-5-yl)tetrazolo[1,5-a]quinoline (120 g) was dissolved in a solution of 22 g of sodium hydroxide and 6 liters of water at 80° C. Powdered charcoal was added to the brown solution which was filtered hot to give a pale yellow clear filtrate. The solution was allowed to cool for 18 hours and the solid which precipitated was separated by filtration and dried to give the sodium salt of 4-(1H-tetrazol-5-yl)tetrazolo[1,5-a]quinoline (2⅓H₂O) melting at about 315°–317° C. with decomposition.

EXAMPLE 17

A mixture of 20 g of 4-(1H-tetrazol-5-yl)tetrazolo[1,5-a]quinoline, 5.1 g of potassium hydroxide and 200 ml of water was heated to 80° C. Charcoal was added and the solution was filtered hot. When the filtrate was cooled, a solid crystallized from the solution. This was separated by filtration to give the potassium salt of 4-(1H-tetrazol-5-yl)tetrazolo[1,5-a]quinoline (⅛H₂O) melting at about 310° C.

EXAMPLE 18

4-(1H-Tetrazol-5-yl)tetrazolo[1,5-a]quinoline (20 g) and 7.4 g of calcium acetate were added to 1800 ml of water and the mixture was heated to 90° C. The solids dissolved slowly and solution was obtained after 2 hours. Charcoal was then added and the solution was filtered hot. The precipitate which formed upon cooling was separated by filtration to give the calcium salt of 4-(1H-tetrazol-5-yl)tetrazolo[1,5-a]quinoline (3.5 H₂O) as a fluffy pink solid melting at greater 310° C.

EXAMPLE 19

A solution was prepared from 20 g of 4-(1H-tetrazol-5-yl)tetrazolo[1,5-a]quinoline, 15 g of tromethamine and 150 ml of water at 80° C. This was treated with charcoal and filtered and the filtrate was cooled. The precipitate which then formed was separated by filtration to give the tromethamine salt of 4-(1H-tetrazol-5-yl)tetrazolo[1,5-a]quinoline as a pale yellow crystalline powder melting at about 263°–264° C. with decomposition.

EXAMPLE 20

4-(1H-Tetrazol-5-yl)tetrazolo[1,5-a]quinoline (20 g) and 14.7 g of triethanolamine were added to 150 ml of water and a clear solution was obtained upon warming to 50° C. The solution was treated with charcoal and filtered hot and the filtrate was diluted with 2-propanol until precipitation began. The solution was then cooled to 0° C. and the solid which formed was separated by filtration to give the triethanolamine salt of 4-(1H-tetrazol-5-yl)tetrazolo[1,5-a]quinoline as a tan powder melting at about 148°–150° C.

EXAMPLE 21

A solution was prepared from 800 g of N-methyl-D-glucamine and 5000 ml of water and 940 g of 4-(1H-tetrazol-5-yl)tetrazolo[1,5-a]quinoline was added. The mixture was heated to 50° C. for 1 hour to bring about solution of the solids. Powdered charcoal (40 g) was added to the homogeneous brown solution and this was filtered to give a clear brown solution. To the filtrate was added 15000 ml of ethanol and the mixture was allowed to stand overnight. A solid crystallized from the solution in the form of fluffy white needles. The solid was collected by filtration, washed with ethanol and dried to give the N-methyl-D-glucamine salt of 4-(1H-tetrazol-5-yl)tetrazolo[1,5-a]quinoline melting at about 153°–155° C.

What is claimed is:

1. A compound of the formula:

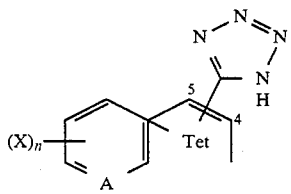

wherein Tet is the divalent tetrazolo group of the formula

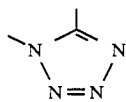

which is attached to the ring system to give either isomeric form; A is —CH= or —N=; n is 0, 1 or 2; X is H, alkyl or 1–4 C, alkoxy of 1–4 C, halogen, methylmercapto, methylsulfonyl, or two X's can be combined as methylenedioxy; with the proviso that, when X is methylmercapto or methylsulfonyl, then n must be 1; or a pharmaceutically acceptable salt thereof.

2. A compound according to claim 1 which has the formula:

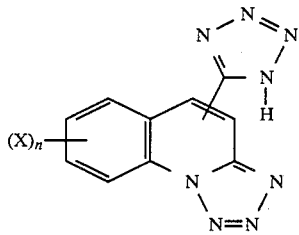

wherein n is 0, 1 or 2; X is hydrogen, alkyl of 1–4 C, alkoxy of 1–4 C, halogen, methylmercapto, methylsulfonyl, or two X's can be combined as methylenedioxy; with the proviso that, when X is methylmercapto or methylsulfonyl, then n must be 1; or a pharmaceutically acceptable salt thereof.

3. A compound according to claim 1 which has the formula:

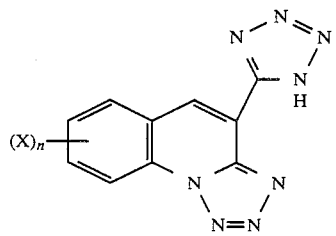

wherein n is 0, 1 or 2; X is hydrogen, alkyl of 1–4 C, alkoxy of 1–4 C, halogen, methylmercapto, methylsulfonyl, or two X's can be combined as methylenedioxy; with the proviso that, when X is methylmercapto or methylsulfonyl, then n must be 1; or a pharmaceutically acceptable salt thereof.

4. A compound according to claim 1 which 4-(1H-tetrazol-5-yl)tetrazolo[1,5-a]quinoline or a pharmaceutically acceptable salt thereof.

5. A compound according to claim 1 which is 4-(1H-tetrazol-5-yl)tetrazolo[1,5-a]quinoline.

6. A compound according to claim 1 which is 4-(1H-tetrazol-5-yl)tetrazolo[1,5-a]quinoline, salt with N-methylglucamine.

7. A compound according to claim 1 which is 7,8-dimethyl-4-(1H-tetrazol-5-yl)tetrazolo[1,5-a]quinoline.

8. A compound according to claim 1 which is 7,8-dimethoxy-4-(1H-tetrazol-5-yl)tetrazolo[1,5-a]quinoline.

9. A compound according to claim 1 which is 5-(1H-tetrazol-5-yl)tetrazolo[1,5-a]quinoline.

10. A compound according to claim 1 which is 5-(1H-tetrazol-5-yl)tetrazolo[5,1-a]isoquinoline.

11. A method for inhibiting the results of antibody-antigen reactions in mammals which comprises administration to a mammal susceptible to allergic reaction of an effective amount of a compound of the formula:

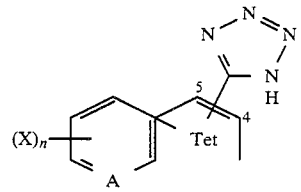

wherein Tet is the divalent tetrazolo group of the formula

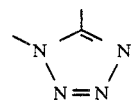

which is attached to the ring system to give either isomeric form; A is —CH= or —N=; n is 0, 1 or 2; X is H, alkyl or 1–4 C, alkoxy of 1–4 C, halogen, methylmercapto, methylsulfonyl, or two X's can be combined as methylenedioxy; with the proviso that, when X is methylmercapto or methylsulfonyl, then n must be 1; or a pharmaceutically acceptable salt thereof.

12. A method according to claim 11 which comprises administration of an effective amount of a compound selected from 4-(1H-tetrazol-5-yl)tetrazolo[1,5-a]quinoline or a pharmaceutically acceptable salt thereof.

13. A method according to claim 11 which comprises administration of an effective amount of 4-(1H-tetrazol-5-yl)tetrazolo[1,5-a]quinoline, salt with N-methylglucamine.

* * * * *

UNITED STATES PATENT AND TRADEMARK OFFICE
CERTIFICATE OF CORRECTION

PATENT NO. : 4,496,569

DATED : January 29, 1985

INVENTOR(S) : Terry L. Wright

It is certified that error appears in the above-identified patent and that said Letters Patent are hereby corrected as shown below:

Column 1, line 15, in the structural formula

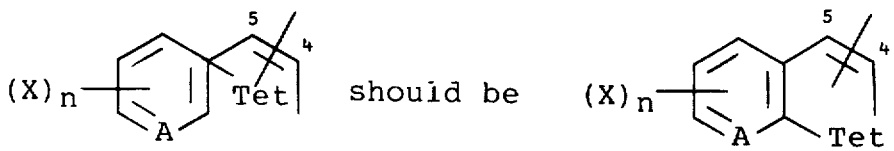

Column 1, line 32, both occurrences of the word "or" should read -- of --.

Column 2, line 36, "meth-Cohn" should read -- Meth-Cohn --.

Column 2, line 63, "[-CH=N$^{\oplus}$<]" should read -- [-CH=N$^{\oplus}$<] --.

Column 6, line 9, "procedure" should read -- product --.

Column 7, line 41, after the phrase "and a heavy" insert the word -- yellow --.

Column 9, line 24, "[5,1-a[" should read -- [5,1-a] --.

Column 9, line 25, "235°-250° C. decomposition" should read -- 235°-250° C. with decomposition --.

Column 10, line 60, in the structural formula

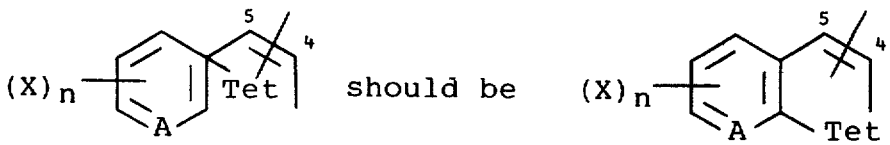

Column 11, line 10, "or" should read -- of --.

UNITED STATES PATENT AND TRADEMARK OFFICE
CERTIFICATE OF CORRECTION

PATENT NO. : 4,496,569
DATED : January 29, 1985
INVENTOR(S) : Terry L. Wright

It is certified that error appears in the above-identified patent and that said Letters Patent are hereby corrected as shown below:

Column 12, line 25, in the structural formula

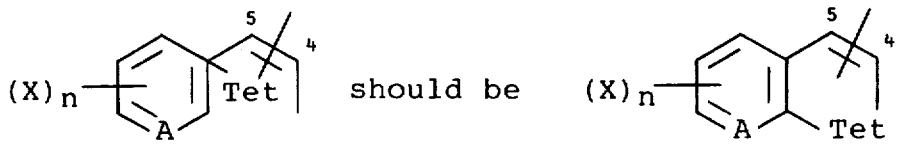

Column 12, line 42, "or" should read -- of --.

Signed and Sealed this

Twenty-fifth Day of June 1985

[SEAL]

Attest:

DONALD J. QUIGG

Attesting Officer

Acting Commissioner of Patents and Trademarks